(12) United States Patent
Tucker

(10) Patent No.: US 7,994,131 B2
(45) Date of Patent: Aug. 9, 2011

(54) STIMULATION OF PROLIFERATION OF PLURIPOTENTIAL STEM CELLS THROUGH ADMINISTRATION OF PREGNANCY ASSOCIATED COMPOUNDS

(75) Inventor: Joseph Tucker, Calgary (CA)

(73) Assignee: Stem Cell Therapeutics Corp., Calgary (CA)

( * ) Notice: Subject to any disclaimer, the term of this patent is extended or adjusted under 35 U.S.C. 154(b) by 357 days.

(21) Appl. No.: 11/246,511

(22) Filed: Oct. 7, 2005

(65) Prior Publication Data
US 2006/0089309 A1 Apr. 27, 2006

Related U.S. Application Data

(60) Provisional application No. 60/616,204, filed on Oct. 7, 2004, provisional application No. 60/661,255, filed on Mar. 10, 2005.

(51) Int. Cl.
*A61K 38/00* (2006.01)
*A61K 38/24* (2006.01)
*A61K 38/18* (2006.01)
*A61P 9/00* (2006.01)
*C12N 5/074* (2010.01)

(52) U.S. Cl. ........ 514/16.4; 514/9.7; 514/7.6; 514/10.1; 424/93.7; 424/93.1

(58) Field of Classification Search .................. None
See application file for complete search history.

(56) References Cited

U.S. PATENT DOCUMENTS

| | | | |
|---|---|---|---|
| 4,062,942 A * | 12/1977 | Donini | 514/12 |
| 5,055,554 A * | 10/1991 | Nomura et al. | 530/313 |
| 5,128,242 A | 7/1992 | Arimura et al. | |
| 5,198,542 A | 3/1993 | Onda et al. | |
| 5,208,320 A | 5/1993 | Kitada et al. | |
| 5,326,860 A | 7/1994 | Onda et al. | |
| 5,506,107 A | 4/1996 | Cunningham et al. | |
| 5,547,935 A | 8/1996 | Mullenbach et al. | |
| 5,610,138 A * | 3/1997 | Jacobs | 514/12 |
| 5,614,184 A | 3/1997 | Sytkowski et al. | |
| 5,623,050 A | 4/1997 | Kitada et al. | |
| 5,700,781 A * | 12/1997 | Harris | 514/21 |
| 5,723,115 A | 3/1998 | Serrero | |
| 5,773,569 A | 6/1998 | Wrighton et al. | |
| 5,801,147 A | 9/1998 | Kitada et al. | |
| 5,837,460 A | 11/1998 | Von Feldt et al. | |
| 5,851,997 A * | 12/1998 | Harris | 514/21 |
| 5,885,574 A | 3/1999 | Elliott | |
| 5,980,887 A * | 11/1999 | Isner et al. | 424/93.7 |
| 6,048,971 A | 4/2000 | Sytkowski et al. | |
| 6,191,106 B1 | 2/2001 | Mullenbach et al. | |
| 6,242,563 B1 | 6/2001 | Dong | |
| 6,333,031 B1 | 12/2001 | Olsson et al. | |
| 6,413,952 B1 | 7/2002 | Luengo et al. | |
| 6,583,109 B1 | 6/2003 | Gallo et al. | |
| 6,844,315 B2 * | 1/2005 | Khan et al. | 514/2 |
| 7,097,832 B1 * | 8/2006 | Kornowski et al. | 424/93.7 |
| 7,183,251 B1 * | 2/2007 | Russo et al. | 514/2 |
| 2002/0098178 A1 | 7/2002 | Brand | |
| 2003/0060415 A1 | 3/2003 | Hung | |

FOREIGN PATENT DOCUMENTS

| | | | |
|---|---|---|---|
| JP | 01180833 A * | 7/1989 | |
| RU | 2003339 C1 * | 11/1993 | |
| WO | WO 96/40231 | 12/1996 | |
| WO | WO 97/48729 | 12/1997 | |
| WO | 199805353 | 2/1998 | |
| WO | WO03018782 | 3/2003 | |
| WO | WO03024472 | 3/2003 | |

OTHER PUBLICATIONS

Definition of pluripotent in the medical dictionary: http://medical-dictionary.thefreedictionary.com/pluripotent; accessed Apr. 15, 2008.*
Nomura et al., Endocrinologia Japonica (1988), 35(3), 413-419 (Abstract only provided).*
Cai et al., NeuroMolecular Medicine, 2002, vol. 2, p. 233-249.*
Nomura et al. Acta Endocrinologica, Oct. 1989;121(4):587-594.*
Scaffidi, Boll Soc Ital Biol Sper. Oct. 15, 1966;42(19):1284-1286.*
"Ischemic Heart Diseas" (Author unknown), http://www.arupconsult.com/Topics/IHD.html#, Accessed May 20, 2010.*
Sugahara et al., PNAS 1995 92 (6)2041-2045.*
Al-Hader AA et al., "Neurons from Fetal Rat Brain Contain Functional Luteinizing Hormone/Chorionic Gonadotropin Receptors" 1997, vol. 56, pp. 1071-1076.
Fernandez-Pol, J.A., "Epidermal Growth Factor Receptor of A431 Cells", J Biol Chem, Apr. 1985, vol. 260, No. 8, pp. 5003-5011.
Johnson, D.L. & Jolliffe L.K., "Erythropoietin mimetic peptides and the future", Nephrol Dial Transplant, 2000, vol. 15, pp. 1274-1277.
Karbanova et al., "Neural Stem Cells Transplanted into Intact Brains As Neurospheres Form Solid Grafts Composed of Neurons, Astrocytes and Oligodendrocyte Precursors", Biomed. Papers, 2004, vol. 148, No. 2, pp. 217-220.
Kaushanksy, K., "Hematopoietic Growth Factor Mimetics" Ann NY Acad Sci, 2001, vol. 938, pp. 131-138.
Livnah., et al., "Functional Mimicry of a Protein Hormone by a Peptide Agonist: The EPO Receptor Complex at 2.8A", Science, Jul. 1996, vol. 273, No. 5274, pp. 464-471.
Mode, A. et al, "The Human Growth Hormone (hGH) Antagonist $^{G120R}$hGH Does Not Antagonize GH in the Rat, But Has Paradoxical Agonist Activity, Probably Via the Prolactin Receptor*", Endocrinology, 1996, vol. 137, No. 2, pp. 447-454.
Moro et al, "Maxadilan, the Vasodilator from Sand Flies, Is a Specific Pituitary Adenylate Cyclase Activating Peptide Type I Receptor Agonist*", J Bio Chem, Jan. 1997, vol. 272, No. 2, pp. 966-970.

(Continued)

Primary Examiner — Jeffrey Stucker
Assistant Examiner — Daniel C Gamett
(74) Attorney, Agent, or Firm — McKeon Meunier Carlin Curfman

(57) ABSTRACT

The present invention provides for a method for stimulating the proliferation of pluripotential stem cells in a mammal comprising administration of pregnancy related compounds more particularly human chorionic gonadotropin, leutenizing hormone or prolactin. The present invention further provides for a method of treatment of tissues or organs experiencing cellular damage, injury or disease.

11 Claims, 7 Drawing Sheets

OTHER PUBLICATIONS

Ogueta S. et al., "Prolactin is a Component of the Human Synovial Liquid and Modulates the Growth and Chondrogenic Differentiation of Bone Marrow-Derived Mesenchymal Stem Cells", Molecular and Cellular Endocrinology 2002, vol. 190, pp. 51-63.

Rodriguez-Pena A., "Oligodendrocyte Development and Thyroid Hormone", J Neurobiol, 1999, vol. 40, pp. 497-512.

Shingo T. et al., "Pregnancy-Stimulated Neurogenesis in the Adult Female Forebrain Mediated by Prolactin", Science, Jan. 2003, vol. 299, pp. 117-120.

Wrighton, N.C., et al., "Small Peptides as Potent Mimetics of the Protein Hormone Erythropoietin", Science, Jul. 1996, vol. 273, No. 5274, pp. 458-463.

DeVito, W.J., et al. "Prolactin-Stimulated Mitogenesis of Cultured Astrocytes*," *Endocrinology* 130(5): 2549-2556 (1992).

English translation of RU 2003339 C1. Russian Federation Committee for Patents and Trademarks. Published Nov. 30, 1993.

English Translation of Bondarenko, P., "*Chorionic Gonadotropin in Treatment of Chronic Circulatory Failure in Patients with Ischemic Heart Disease*", Vrach Delo. 1984, vol. 7, pp. 75-78.

Urbanek et al., "*Stem cell niches in the adult mouse heart*", PNAS, Jun. 13, 2006, V. 103, pp. 9226-9231.

Gage, Fred H. and Verman, Inder M. "Stem cells at the dawn of the 21st century," PNAS vol. 100, sup 1: 11817-11818, Sep. 30, 2003.

Thorne, Rick F. et al. "The role of the CD44 transmembrane and cytoplasmic domains in co-ordinating adhesive and signalling events," Journal of Cell Science 117: 373-380, 2004.

Watt, Fiona M. and Hogan, Brigid L.M. "Out of Eden: Stem Cells and Their Niches," Science vol. 287: 1427-1430, Feb. 25, 2000.

XP-002587374 Definition of "Stem Cell" from Wikipedia. Retrieved from "http://web.archive.org/web/20040924012115/http://en.wikipedia.org/wiki/Stem_cell" Printed Jun. 16, 2010.

Abstract of DE19905961 Al, "Use of estrogens to treat cardiac insufficiency and left ventricular dysfunction following myocardial infarction," Aug. 17, 2000.

Database EPODOC European Patent Office, The Hague, NL; Jul. 18, 1998, XP002626863, Database accession No. JP1180833 abstract & JP 1 180833 A (Nippon Kayaku KK) Jul. 18, 1989.

Partial European Search Report in related European Application No. 11000912.3-1521. Apr. 12, 2011.

* cited by examiner

Increase of BrdU Incorporation by Cells in Rat Liver Tissue Treated With HCG

Increase of BrdU Incorporation by Cells in Male Mouse Heart Tissue

Increase of BrdU Incorporation by Cells in Female Mouse Heart Tissue

Increase of BrdU Incorporation by Cells in Male Mouse Liver Tissue

Increase of BrdU Incorporation by Cells in Female Mouse Liver Tissue

Increase of BrdU Incorporation by Cells in Male Mouse Kidney Tissue

Increase of BrdU Incorporation by Cells in Female Mouse Kidney Tissue

STIMULATION OF PROLIFERATION OF PLURIPOTENTIAL STEM CELLS THROUGH ADMINISTRATION OF PREGNANCY ASSOCIATED COMPOUNDS

RELATED APPLICATIONS

This application claims the benefit of U.S. Provisional Application Ser. No. 60/616,204, filed Oct. 7, 2004 and 60/661,255 filed Mar. 10, 2005, which are hereby incorporated by reference in their entirety.

FIELD OF THE INVENTION

The present invention relates to a method of stimulating stem-cell production in a mammal, specifically a method to increase proliferation of cells in tissues of a mammal, in particular the heart, liver and kidney.

BACKGROUND OF THE INVENTION

In mammals, stem cells represent a category of cells capable of replication of themselves, with the capability to further differentiate to a cell capable of performing a specific function, for example a liver cell, neuron, leukocyte, etc. The key feature of those cells referred to as stem cells is the ability to self-renew or replicate more of themselves, with the pluripotential stem cells capable of differentiating into one of a number of terminally differentiated cells. It is believed that the role of stem cells is to replace those cells otherwise lost to death, disease or injury. That is, upon injury or disease, it is contemplated that the pluripotential stem cells otherwise present or near the site of injury or disease are capable of differentiating into a cell capable of replacing the diseased or injured cell(s).

Currently the art is directed to a multitude of aspects of stem cell research, one of which is to better understand and control the process of differentiation. Stem cells are observed to be present in nearly all tissues and organs of the body, in varying amounts. As well, stem cells are normally present in low amounts in the blood and lymphatic system of mammals, thereby presenting systemic access of stem cells in a mammal.

It is currently contemplated in the art that if one of the natural roles of a stem cell in a mammal is to replace those injured or diseased cells, introduction of stem cells to a tissue or organ that is suffering from disease or injury may enable the repair and/or otherwise implement the alleviation of the disease state. Yet, the isolation and later introduction of stem cells into a patient in need of treatment can be a complex and expensive process, with the potential for the introduced stem cells to be altered and affected by the isolation procedure. Therefore there exists a need to increase the presence of stem cells in a tissue or organ in need of treatment without resorting to isolation and introduction procedures.

SUMMARY OF THE INVENTION

The present invention relates to the stimulation of proliferation of pluripotential stem cells in a tissue or organ of a mammal through administration of pregnancy related compounds, specifically prolactin, LH or HCG. More particularly, the present invention provides for the use of LH, HCG or prolactin, independently, in combination, or in combination or association with additional agents, for stimulation of proliferation of pluripotential stem cells in a tissue or organ.

Accordingly, one aspect of the present invention provides novel methods to stimulate the proliferation of pluripotential stem cells in a mammal. In a further aspect, the present invention provides novel methods to stimulate the proliferation of pluripotential stem cells in specific tissues of a mammal including the heart, liver and kidney.

In another aspect, the present invention provides novel methods to replace damaged or diseased cells in a tissue or organ in a mammal, through stimulation of proliferation of pluripotential stem cells in the tissue or organ enabling a larger population of stem cells to differentiate into the cells in need of replacement. In a further aspect, the present invention provides novel methods to replace damaged to diseased cells in tissues or organs including heart, kidney or liver, through stimulation of proliferation of pluripotential stem cells in the tissue or organs including heart, kidney or liver by enabling a larger population of stem cells to differentiate into the cells in need of replacement.

In another aspect the present invention provides for methods of treatment of organ disease or damage in a mammal comprising daily administration of an effective amount of LH, HCG or prolactin, independently, in combination, or in combination or association with additional agents. In a further aspect, the organ disease or damage is present a human and in organs including the heart, liver or kidney. In a further aspect, the administration of the HCG or prolactin comprises a daily administration of 75-300 µg per day, more preferably 100-200 µg per day, even more preferably 140 µg per day. In a further aspect, the HCG or prolactin is administered daily for 7 days.

In another aspect the present invention provides for methods of treatment of organ disease or damage in a mammal comprising single administration of an effective amount of LH, HCG or prolactin, independently, in combination, or in combination or association with additional agents. In a further aspect, the organ disease or damage is present in a human and in organs including the heart, liver or kidney. In a further aspect, the administration of the HCG or prolactin comprises a single administration of 2,000-10,000 IU, more preferably 2000-4000 IU, even more preferably 3000 IU.

In another aspect the present invention provides for a method to stimulate the proliferation of pluripotential stem cells systemically in a mammal comprising the administration to the mammal of pregnancy related compounds in sufficient amount to induce the proliferation of pluripotential stem cells. A further aspect of the present invention provides for a method to stimulate the proliferation of cells systemically in a mammal comprising the administration to the mammal of pregnancy related compounds in sufficient amount to induce the proliferation of pluripotential stem cells wherein the pregnancy related compound is independently selected from the group comprising prolactin, Human Chorionic Gonadotropin (HCG or hCG), and Leutinizing Hormone (LH).

Whether the prolactin, LH or HCG is used in vivo or in vitro, other agents may be applied in combination, such as follicle-stimulating hormone (FSH), gonadotropin releasing hormone (GnRH), prolactin releasing peptide (PRP), erythropoietin, pituitary adenylate cyclase activating polypeptide (PACAP), serotonin, bone morphogenic protein (BMP), epidermal growth factor (EGF), transforming growth factor alpha (TGFalpha), transforming growth factor beta (TGF-beta), fibroblast growth factor (FGF), estrogen, growth hormone, growth hormone releasing hormone, insulin-like growth factors, leukemia inhibitory factor, ciliary neurotrophic factor (CNTF), brain derived neurotrophic factor (BDNF), thyroid hormone, thyroid stimulating hormone, and/or platelet derived growth factor (PDGF). The prolactin, LH or HCG may be any prolactin, LH or HCG analog or variant which has the activity of the native prolactin, LH or HCG.

An aspect of the present invention provides for a method to identify genes involved proliferation of pluripotential stem cells comprising:
a) isolation of pluripotential stem cells from a mammal;
b) administration of pregnancy related compounds to the isolated pluripotential stem cells for a period of time sufficient to induce proliferation of pluripotential stem cells;
c) preparation of cDNA from the isolated pluripotential stem cells of step "b";
d) preparation of cDNA from the isolated pluripotential stem cells of step "a";
e) removal of cDNA common between the cDNA of step "c" and step "d" through subtractive hybridization; and
f) characterization of the remaining cDNA.

A further aspect of the present invention provides for a method to identify genes involved in proliferation of pluripotential stem cells comprising:
a) isolation of pluripotential stem cells from a mammal;
b) administration of prolactin, HCG or LH to the isolated pluripotential stem cells for a period of time sufficient to induce proliferation of pluripotential stem cells;
c) preparation of cDNA from the isolated pluripotential stem cells of step "b";
d) preparation of cDNA from the isolated pluripotential stem cells of step "a";
e) removal of cDNA common between the cDNA of step "c" and step "d" through subtractive hybridization; and
f) characterization of the remaining cDNA.

An aspect of the present invention provides for a method to identify regulatory factors in pregnancy related compounds involved in proliferation of pluripotential stem cells comprising:
a) isolation of pluripotential stem cells from a mammal;
b) administration of a substantially pure preparation of a known pregnancy related compound; and
c) determination of the presence of increased proliferation or proliferative capacity of the pluripotential stem cells.

A further aspect of the present invention provides for a method to identify regulatory factors in pregnancy related compounds involved in proliferation of pluripotential stem cells comprising:
a) isolation of pluripotential stem cells from a mammal;
b) administration of a substantially pure preparation of prolactin; HCG or LH; and
c) determination of the presence of increased proliferation or proliferative capacity of the pluripotential stem cells.

A further aspect of the present invention provides for a method of treatment of organ disease or damage comprising:
a) administration of stem cells to the organ affected by disease or damage followed by, or preceded by, administration of pregnancy related compound or compounds to the organ or tissue in an effective amount to simulate the proliferation of cells in said organ or tissue.

A further aspect of the present invention provides for a method of treatment of organ disease or damage comprising:
a) administration of stem cells to the organ affected by disease or damage followed by, or preceded by, administration of prolactin, HCG or LH to the organ or tissue in an effective amount to simulate the proliferation of cells in said organ or tissue.

The accompanying description illustrates preferred embodiments of the present invention and serves to explain the principles of the present invention.

DETAILED DESCRIPTION OF THE INVENTION

Figure 1:
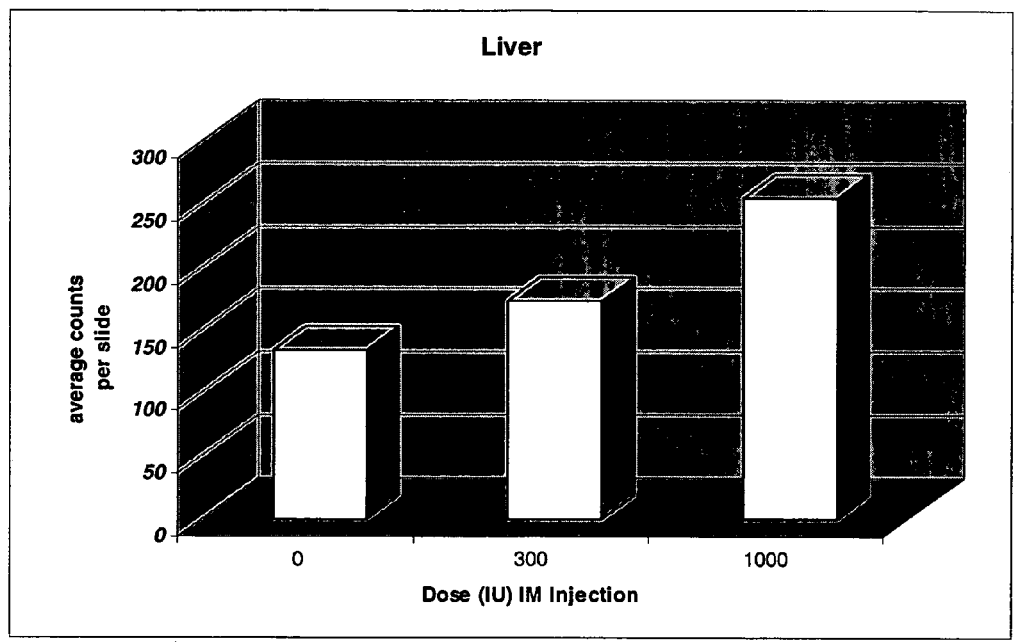
FIG. 1 shows the observed increase in average BrdU incorporation per slide observed in male and female rat liver tissue sections.

As used herein, the following terms have the following definitions:

As used herein, "administration" means the introduction of a compound to a mammal, either systemically or localized to an organ or tissue, through means generally known in the art, such that the administered compound is capable of interacting with the general tissue or organ, or cells of interest. Examples of such means generally known in the art include, but are not limited to, oral formulations, intravenous injection, catheterization, suppository, and direct introduction to a tissue through injection.

As used herein, "pregnancy related compounds" mean compounds specifically produced, either constitutively or transitively, during pregnancy of a mammal. Compounds include, but are not limited to, those compounds which are normally present in a mammal but are found in increased concentration in a pregnant mammal.

As used herein "disease" means a state in a mammal which may directly or indirectly lead to a cellular, tissue, organ or systemic state detrimental to the mammal.

As used herein, "pluripotential stem cell" means a cell capable of reproducing itself and capable of terminal differentiation into a cell-type normally found in the relevant mammalian system, tissue or organ.

As used herein, "proliferation of cells" means the increase in reproduction, including but not limited to mitotic events, in a cell. An increase in proliferation of cells is not limited to an increase in proliferative rate or increase in reproduction, but also includes an alteration of cells not normally capable of reproduction such that they are capable and actively undergo reproduction and/or mitotic events.

A polypeptide which shares "substantial sequence similarity" with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level.

The phrase "percent identity" or "% identity" of an analog or variant with a native factor refers to the percentage of amino acid sequence in the native factor which are also found in the analog or variant when the two sequences are aligned.

Percent identity can be determined by any methods or algorithms established in the art, such as LALIGN or BLAST.

A polypeptide possesses a "biological activity" of a native factor if it is capable of binding to the receptor for the native factor or being recognized by a polyclonal antibody raised against the native factor. Preferably, the polypeptide is capable of specifically binding to the receptor for the native factor in a receptor binding assay.

A "functional agonist" of a native factor is a compound that binds to and activates the receptor of the native factor, although it does not necessarily share a substantial sequence similarity with the native factor.

An "LH" is a protein which
(1) comprises a polypeptide that shares substantial sequence similarity with a native mammalian LH, preferably the native human LH; and
(2) possesses a biological activity of the native mammalian LH.

The native mammalian LH is a gonadotropin secreted by the anterior lobe of the pituitary. LH is a heterodimer consisting of non-covalently bound alpha and beta subunits. The alpha subunit is common among LH, FSH and hCG, and the beta subunit is specific for each hormone. The LH useful in the present invention may have the native alpha subunit, with the beta subunit sharing a substantial sequence similarity with a native mammalian LH. Alternatively, the LH may have the native beta subunit, with the alpha subunit sharing a substantial sequence similarity with a native mammalian LH. The LH may also have both the alpha and beta subunit sharing a substantial sequence similarity with a native, corresponding subunit. Thus, the term "LH" encompasses LH analogs which comprise a deletional, insertional, or substitutional mutants of a native LH subunit. Furthermore, the term "LH" encompasses the LHs from other species and the naturally occurring variants thereof. In addition, an "LH" may also be a functional agonist of a native mammalian LH receptor.

An "HCG" is a protein which (1) comprises a polypeptide that shares substantial sequence similarity with the native HCG; and (2) possesses a biological activity of the native HCG. The native HCG is a heterodimer consisting of non-covalently bound alpha and beta subunits. The alpha subunit is common among LH, FSH and HCG, and the beta subunit is specific for each hormone. However, the beta subunits of HCG and LH shares a 85% sequence similarity. The HCG useful in the present invention may have the native alpha subunit, with the beta subunit sharing a substantial sequence similarity with the native HCG. Alternatively, the HCG may have the native beta subunit, with the alpha subunit sharing a substantial sequence similarity with the native HCG. The HCG may also have both the alpha and beta subunit sharing a substantial sequence similarity with the native, corresponding subunit. Thus, the term "HCG" encompasses HCG analogs which comprise a deletional, insertional, or substitutional mutants of a native HCG subunit. Furthermore, the term "HCG" encompasses the HCG counterparts from other species and the naturally occurring variants thereof. In addition, an "HCG" may also be a functional agonist of a native mammalian HCG/LH receptor.

A "prolactin" is a polypeptide which (1) shares substantial sequence similarity with a native mammalian prolactin, preferably the native human prolactin; and (2) possesses a biological activity of the native mammalian prolactin. The native human prolactin is a 199-amino acid polypeptide synthesized mainly in the pituitary gland. Thus, the term "prolactin" encompasses prolactin analogs which are the deletional, insertional, or substitutional mutants of the native prolactin. Furthermore, the term "prolactin" encompasses the prolactins from other species and the naturally occurring variants thereof.

In addition, a "prolactin" may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode, A. et al *Endocrinology* 137:447 (1996)); or a ligand for the prolactin receptor as described in U.S. Pat. Nos. 5,506,107 and 5,837,460; all of which are herein incorporated by reference.

An "EGF" means a native EGF or any EGF analog or variant that shares a substantial amino acid sequence similarity with a native EGF, as well as at least one biological activity with the native EGF, such as binding to the EGF receptor. Particularly included as an EGF is the native EGF of any species, TGF-α, or recombinant modified EGF. Specific examples include, but are not limited to, the recombinant modified EGF having a deletion of the two C-terminal amino acids and a neutral amino acid substitution at position 51 (particularly EGF51 gln51; U.S. Patent Application Publication No. 20020098178A1, herein incorporated by reference), the EGF mutein (EGF-X.sub.6) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935 all of which are herein incorporated by reference.

In addition, an "EGF" may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, *J. Biol Chem* 260:5003 (1985) and U.S. Pat. No. 5,723,115, herein incorporated by reference).

A "PACAP" means a native PACAP or any PACAP analog or variant that shares a substantial amino acid sequence similarity with a native PACAP, as well as at least one biological activity with the native PACAP, such as binding to the PACAP receptor. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563 herein incorporated by reference.

In addition, a "PACAP" may also be a functional agonist of a native mammalian PACAP receptor. For example, the functional agonist may be maxadilan, a polypeptide that acts as a specific agonist of the PACAP type-1 receptor (Moro et al *J. Biol Chem* 272:966 (1997)).

An "erythropoietin (EPO)" means a native EPO or any EPO analog or variant that shares a substantial amino acid sequence similarity with a native EPO, as well as at least one biological activity with the native EPO, such as binding to the EPO receptor. Erythropoietin analogs and variants are disclosed, for example, in U.S. Pat. Nos. 6,048,971 and 5,614,184, herein incorporated by reference.

In addition, an "EPO" may also be a functional agonist of a native mammalian EPO receptor. For example, the functional agonist may be EMP1 (EPO mimetic peptide 1, Johnson, D. L. et al *Nephrol Dial Transplant* 15:1274 (2000)); one of the short peptide mimetics of EPO as described in Wrighton, N. C. et al *Science* 273:458 (1996) and U.S. Pat. No. 5,773,569; any small molecular EPO mimetic as disclosed in Kaushansky, K. *Ann NY Acad Sci* 938:131 (2001); an antibody that activates the EPO receptor as described in U.S. Pat. No 5,885,574, WO 96/40231, WO 97/48729, Fernandez-Pol, *J. Biol Chem* 260:5003 (1985) or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952, herein incorporated by reference), or a ligand for the EPO receptor as described in U.S. Pat. Nos. 5,506,107 and 5,837,460, all of which are herein incorporated by reference.

An "effective amount" is an amount of a therapeutic agent sufficient to achieve the intended purpose. For example, an effective amount of an LH or HCG to increase the number of neural stem cells is an amount sufficient, in vivo or in vitro, as the case may be, to result in an increase in neural stem cell number. An effective amount of an LH or HCG to treat or ameliorate a neurodegenerative disease or condition is an amount of the LH/HCG sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

The present invention provides for the use of pregnancy related hormones, which include but are not limited to the pregnancy related compounds prolactin, HCG, LH and estrogen, in a substantially pure preparation; to stimulate the proliferation of pluripotential stem cells in tissues other than the brain. Alternatively the present invention provides for the use of pregnancy related compounds in a mammal, which include but are not limited to ovarian hormones, prolactin, HCG, LH and estrogen in combination with other pregnancy related compounds, or compounds known in the art to stimulate pluripotential stem cells or otherwise encourage or cause the differentiation of the pluirpotential stem cells.

The mammal can optionally receive at least one additional agent, such as erythropoietin, cyclic AMP, pituitary adenylate cyclase activating polypeptide (PACAP), serotonin, bone morphogenic protein (BMP), epidermal growth factor (EGF), transforming growth factor alpha (TGF.alpha.), fibroblast growth factor (FGF), estrogen, growth hormone, insulin-like growth factor 1, and/or ciliary neurotrophic factor (CNTF).

The prolactin, HCG, LH and/or the additional agent can be provided by any method established in the art. For example, they can be administered intravascularly, intrathecally, intravenously, intramuscularly, subcutaneously, intraperitoneally, topically, orally, rectally, vaginally, nasally, by inhalation or into the brain. The administration is preferably performed systemically, particularly by subcutaneous administration. The prolactin, HCG, LH or additional agent can also be provided by administering to the mammal an effective amount of an agent that can increase the amount of endogenous prolactin, HCG, LH or the additional agent in the mammal. For example, the level of LH in an animal can be increased by using GnRH.

Accordingly, the present invention provides a method of increasing neural stem cells numbers either in vivo or in vitro using a prolactin, HCG, or LH. HCG is expected to have the same effect as LH as HCG is an analog of, and shares the same receptor with, LH. When used to increase stem cell number in an organ or tissue in vivo, this method will result in a larger pool of stem cells in the organ or tissue. This larger pool of stem cells can subsequently generate more differentiated cells appropriate for the organ or tissue, than would a population of stem cells without prolactin, HCG, or LH. The cells, in turn, can compensate for lost or degenerate cells which are associated with organ disease or damage or tissue disease or damage.

Prolactin, HCG, or LH or other factors induced by these compounds can also be used to increase stem cell numbers in vitro. The resulting stem cells can be used to produce more organ specific cells in vitro, or used in transplantation procedures into humans or animals suffering from diseases or conditions associated with organ disease or damage. It is preferable that stem cells produced according to the present invention, rather than organ specific cells, are transplanted. Once stem cells are transplanted, growth and/or differentiation agents can be administered in vivo to further increase the number of stem cells, or to selectively enhance organ specific cell formation. The additional agents can likewise be used in vitro with prolactin, HCG, or LH, or administered in vivo in combination with prolactin, HCG, or LH.

Exemplary differentiation agents include, but are not limited to:

1. Erythropoeitin (Epo): It has been demonstrated that Epo enhances stem cell commitment to a cell lineage.
2. Transforming growth factor beta and bone morphogenetic proteins (BMPs): BMPs are known differentiation agents.
3. Thyroid hormone (TH, including both the T3 and T4 forms): TH is known as a differentiation agent. See for example Rodriguez-Pena A. *J Neurobiol* 40(4):497 (1999).
4. Thyroid stimulating hormone (TSH) and Thyroid releasing hormone (TRH): TSH/TRH promote the release of TH from the anterior pituitary resulting in increased levels of circulating TH.

Agents that can increase stem cell number include, without being limited to:

1. Follicle-stimulating hormone (FSH) often acts in concert with LH; known to induce LH receptor expression and can therefore enhance the effects of LH signaling.
2. Growth hormone (GH) can stimulate stem cell proliferation.
3. Insulin growth factors (IGFs) are somatomedians that are released from many tissues in response to GH and mediate many of the growth promoting effects of GH.
4. Growth hormone releasing hormone (GHRH) are secreted from the hypothalamus and induces GH release from the anterior pituitary, resulting in increased levels of circulating GH.
5. Fibroblast growth factor is a known mitogenic agent for stem cells.
6. Epidermal growth factor is a known mitogenic agent for stem cells.
7. Transforming growth factor alpha (TGF-$\alpha$) is a known mitogenic agent for stem cells.
8. Gonadotropin releasing hormone (GnRH) triggers the release of LH and could be used in combination with or in place of prolactin, HCG, or LH to increase circulating levels of LH and enhance stem cell proliferation.

The increase in stem cells or organ specific cells is preferably at least about 10%, more preferably at least about 20%, even more preferably at least about 30%, yet more preferably at least about 40%, still more preferably at least about 50%, and further more preferably at least about 60%. Most preferably, the increase is at least about 80%. As disclosed more fully in Example 2 below, an increase of over 300% in specific organs, such as the kidney, is contemplated.

The present invention also provides a method for treating or ameliorating a disease or condition in an animal, particularly a mammal, characterized by organ or tissue damage. This can be achieved, for example, by administering an effective amount of prolactin, HCG, or LH to the mammal, or transplanting to the mammal stem cells, progenitor cells derived from organ specific stem cells, or organ specific cells produced according to the present invention. Preferably, stem cells are transplanted. In addition to the transplantation, prolactin, HCG, or LH and/or additional agents can be further provided to the transplantation recipient, particularly concurrently with or after the transplantation.

Explicitly contemplated in the present invention is a method for treating or ameliorating a disease or condition in an animal, particularly a mammal, characterized by organ or tissue damage, wherein the organ or tissue is selected from the group comprising heart, liver, spleen, bone, kidney and retina. Alternatively, the present invention may be useful in treatment of Type I Diabetes, spinal injuries, nerve damage, pulmonary disease, reproductive disorders, or any other disease or disorder in which replenishment of tissue or organ cells is beneficial to the treatment or ameliorating the disease or condition.

The prolactin, HCG, or LH useful in the present invention includes any prolactin, HCG, or LH analog or variant which is capable of increasing neural stem cell number. A prolactin, HCG, or LH analog or variant comprises a protein which contains at least about 30% of the amino acid sequence of at least one subunit of the native human prolactin, HCG, or LH; and which possesses a biological activity of the native prolactin, HCG, or LH. Preferably, the biological activity of prolactin, HCG, or LH is the ability to bind the prolactin, HCG, or LH receptors. Specifically included as prolactin, HCG, or LH are the naturally occurring prolactin, HCG, or LH variants; prolactin, HCG, or LH counterparts from various mammalian species, including but not limited to, human, other primates, rat, mouse, sheep, pig, and cattle; and the commonly used analogs listed in Table I below. GnRH, or an analog thereof, can be used in the place of or in addition to prolactin, HCG, or LH.

TABLE 1

Common Analogs of GnRH, LH and hCG

GnRH/LHRH agonists

GnRH agonist, leuprorelin
(pGlu-His-Trp-Ser-Tyr-D-Leu-Leu-Arg-Pro-NHEt)  (SEQ ID NO: 1)
Buserelin another LH-RH agonist
Serophene: A prescription medication that initiates the release of GnRH
LH Luveris ® (lutropin alfa) pure luteinizing hormone
(recombinant human LH)
HCG Ovidrel ®/Ovitrelle ® 1 (choriogonadotropin alfa);
recombinant chorionic gonadotropin (r-hCG)

TABLE 1-continued

Common Analogs of GnRH, LH and hCG

Pregnyl ® is an injectable, highly purified preparation of human chorionic gonadotropin obtained from the urine of pregnant women. Pregnyl has been in use throughout the world since 1932.
NOVAREL ™ (chorionic gonadotropin for injection, USP)
Profasi: human chorionic gonadotropin (hCG). Profasi is administered intramuscularly.

Similarly, any additional compounds or agents that are useful in the present invention include their analogs and variants that share a substantial similarity and at least one biological activity with the native compounds or agents. These additional agents are contemplated to be used in association with prolactin, LH or HCG (or their functional agonists or biological equivalents) to enhance the increase in pluripotential stem cells or organ specific cells in a tissue or to encourage or cause differentiation of the stem cells into the desired cell types.

For example, EGF can be used in conjunction with prolactin, HCG, or LH in the present invention. In addition to native EGF, an EGF analog or variant can also be used, which should share a substantial amino acid sequence similarity with the native EGF, as well as at least one biological activity with the native EGF, such as binding to the EGF receptor. Particularly included as an EGF is the native EGF of any species, TGF-α, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1 herein incorporated by reference), the EGF mutein (EGF-X16) in which the His residue at position 16 is replaced with a neutral or acidic amino acid (U.S. Pat. No. 6,191,106 herein incorporated by reference), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935; all of which are herein incorporated by reference.

As another example, PACAP can also be used in conjunction with LH/hCG. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563; all of which herein incorporated by reference.

Erythropoietin analogs and variants are disclosed, for example, in U.S. Pat. Nos. 6,048,971 and 5,614,184, herein incorporated by reference.

Further contemplated in the present invention are functional agonists of prolactin, HCG, or LH or additional agents useful in the present invention. These functional agonists bind to and activate the receptor of the native agent, although they do not necessarily share a substantial sequence similarity with the native agent. For example, maxadilan is a polypeptide that acts as a specific agonist of the PACAP type-1 receptor (Moro et al *J Biol Chem* 272:966 (1997)).

Functional agonists of EPO have been extensively studied. EMP1 (EPO mimetic peptide 1) is one of the EPO mimetics described in Johnson, D. L. et al *Nephrol Dial Transplant* 15:1274 (2000). Short peptide mimetics of EPO are described in, e.g., Wrighton, N. C. et al *Science* 273:464 (1996) and U.S. Pat. No. 5,773,569, herein incorporated by reference. Small molecular EPO mimetics are disclosed in, e.g., Kaushansky, K. *Ann NY Acad Sci* 938:131 (2001). Antibodies that activate the EPO receptor are described in, e.g., U.S. Pat. No. 5,885,574, herein incorporated by reference; WO 96/40231 and WO 97/48729).

Antibodies that have agonist activities for the EGF receptor are described, e.g., in Fernandez-Pol, *J Biol Chem* 260:5003 (1985) and U.S. Pat. No. 5,723,115, herein incorporated by reference. In addition, activating amino acid sequences are also disclosed in U.S. Pat. No. 6,333,031, herein incorporated by reference, for the EPO receptor, EGF receptor, prolactin receptor and many other cell surface receptors; metal complexed receptor ligands with agonist activities for the prolactin and EPO receptors can be found in U.S. Pat. No. 6,413,952, herein incorporated by reference. Other methods of identifying and preparing ligands for receptors, e.g., EPO and prolactin receptors, are described, for example, in U.S. Pat. Nos. 5,506,107 and 5,837,460, both herein incorporated by reference.

Commonly used analogs of certain additional agents can also be found in Table 2 below:

TABLE 2

Common Analogs of Additional Agents

FSH

Follitropin beta; Follistim/Puregon ®, recombinant follicle-stimulating hormone (FSH), pure gonadotropin widely used to treat infertility; launched by Organon in 1996
GONAL-f ™ (follitropin alpha) is recombinant human follicle-stimulating hormone, which is equivalent in its structure to the naturally occurring human FSH in the body.
BRAVELLE ™ (urofollitropin for injection, purified); highly purified human-derived FSH (Hfsh) only human-derived FSH approved for both subcutaneous (SC) and intramuscular (IM) injection.
PRP (prolactin releasing peptide)

hPRP Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-Gly-Arg-Phe-NH2 (SEQ ID NO: 2)

LIF

Emfilermin (r-LIF) embryo implantation failure: still in clinical studies (NOT YET APPROVED)

EPO

NeoRecormon; Erythropoietin beta; Roche
Epoetin omega; Baxter International Inc.; physico-chemical characteristics different from other erythropoietins or Epos (alpha and beta); currently approved for sale in 15 countries outside of the United States and Western Europe.
darbepoietin

TH

Armour Thyroid, natural desiccated thyroid hormone replacement drug, Forest Pharmaceuticals
Cytomel, synthetic liothyronine sodium (T3), King Pharmaceuticals
Levothroid, synthetic levothyroxine, Forest TABLE 2-continued Common Analogs of Additional Agents Pharmaceuticals (currently not FDA approved as of December 2003)
Levoxyl, synthetic levothyroxine, from King Pharmaceuticals
Nature-throid and Westhroid, natural desiccated thyroid hormone replacement drug, Western Research Laboratories
Synthroid, synthetic levothyroxine, from Abbott Laboratories
Thyrolar, synthetic liotrix, a combination of L-triiodothyronine (T3) and levothyroxine sodium (T4)
Unithroid, synthetic levothyroxine, from Jerome Stevens Pharmaceuticals

TSH

Thyrogen, a synthetic thyroid stimulating hormone (TSH) for use in thyroid cancer patients, from Genzyme Pharmaceuticals, currently FDA approved
TRH (thyroid releasing hormone)

pGlu-His-Pro Amide
THYREL ® TRH (protirelin)

It should be noted that the effective amount of each analog, variant or functional agonist may be different from that for the native agent or compound, and the effective amount in each case can be determined by a person of ordinary skill in the art according to the disclosure herein. Preferably, the native agents, or analogs and variants that share substantial sequence similarity with the native agents, are used in the present invention.

Pharmaceutical compositions are also provided, comprising an prolactin, HCG, or LH, an additional agent as described above, and a pharmaceutically acceptable excipient and/or carrier.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally. Preferably, the composition is delivered into the organ or tissue by injection or infusion. Alternatively, the composition is preferably delivered by systemic routes, such as subcutaneous administration. For example, it has been discovered that prolactin, growth hormone, IGF-1, PACAP and EPO can be effectively delivered by subcutaneous administration to modulate the number of neural stem cells in the subventricular zone of the brain, establishing their ability to affect organs through systemic administration.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insulation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in Remington's Pharmaceutical Sciences.

The following examples are intended to illustrate, though not limit, the scope of the present invention.

EXAMPLE 1

Single Dose Ranging of Leutinizing Hormone(LH)/Human Chorionic Gonadotropin (HCG) In Rats This study was performed to demonstrate the optimal dose of HCG to be used for therapeutic neurogenesis in a stroke model of the rat. Single doses of HCG=[0, 3, 10, 30, 100, 300, 1000, 3000 I.U.] (Sigma C6322, 10,000 IU per mg) were dissolved in 0.5 ml saline solution. Samples of test solutions (0.2 ml) were saved for the purpose of validating concentrations of pre-treatment hormone activity and stored on ice until the time of bioanalytical testing.

Prior to injections, blood samples of 0.5 ml were collected into heparin-Na collecting tubes, centrifuged and frozen (−20 C.), to establish baseline plasma concentrations of hormone. All doses of HCG were injected in 200 g rats (n=2) once intramuscularly (IM). In all rats, a single 0.5 ml blood sample was collected into a sodium-heparin collecting tube, at 60 minutes after injection. The blood was centrifuged at 3000 r.p.m., at 4C. for 10 minutes, within half an hour after sampling.

Twenty four hours after the hormone injection, Bromodeoxyuridine (BrdU) labeling begins. All treated rats (Charles-River, Laval, QC) are injected with BrdU (Sigma) (120 mg/kg, i.p., dissolved in 0.007% NaOH in phosphate buffer) every 2 hr for 10 hr. Animals are sacrificed 24 hours after the first BrdU injection. Brain, heart, kidney, and liver and skin (1 cm2) is preserved. Heart and liver was processed for immunohistochemistry as described below. Plasma and solution samples were stored frozen at −20 C. until time of testing.

Animals are sacrificed by anesthetic overdose and perfused transcardially with 4% paraformaldehyde in PBS, pH 7.2. Brain, heart, liver, kidney, skin and smooth muscle is post-fixed in the perfusing solution overnight at 4° C., and then cryoprotected for at least 24 hr in 20% sucrose in PBS. Brain, heart, liver, kidney, skin and smooth muscle tissue are embedded in Tissue Tek O.C.T. compound (Sakura Finetek, Torrance, Calif.) before they are cryosectioned at 14 µm. Before immunohistochemistry, sections are postfixed with acetone for 30 sec at room temperature, then washed with PBS. For BrdU staining, tissues are treated with 1 M HCl for 30 min at 60° C. to denature cellular DNA. Rat monoclonal anti-BrdU (1:50, Harlan Seralab, Loughborough, UK) and rabbit anti-Ki67 (1:500, Novocastra, Newcastle upon Tyne, UK) are used for detection of proliferating cells. Sections are incubated for 24 hr at 4° C. in primary antibody diluted in 0.3% Triton X-100/PBS containing NGS, washed with PBS, and then incubated with donkey biotinylated secondary antibodies (all used at 1:200, Jackson ImmunoResearch) for 1 hr at room temperature followed by incubation with streptavidin-Cy3 (1:2000, Jackson ImmunoResearch) for 1 hr at room temperature, together with Hoechst 33258 (0.015 mg/ml stock solution diluted to 0.001 mg/ml, Sigma. After rinsing with water, sections are mounted with Fluorosave or other mounting medium with low autofluorescence and viewed or photographed with an appropriate (eg. Zeiss Axiophot) fluorescence microscope.

As shown in FIG. 1, increasing amounts of administered HCG resulted in increased incorporation of BrdU in liver cells, which correlates with increased proliferation of stem cells in the tissue. Incorporation of BrdU in cells resident in heart tissue was maximal at 300 IU of HCG administered, with reduced incorporation in heart cells observed with 1000 IU HCG administered. As allometric scaling form mouse to human is approximately scaled by a factor of 10, preferred administration of 3000 IU of HCG for increased proliferation of stem cells in heart tissue is contemplated, with 3000 IU to 10,000 IU for increased proliferation of stem cells in liver tissue contemplated.

EXAMPLE 2

Stimulating stem cell proliferation by prolactin and human chorionic gonadotropin (HCG) in mice.

A total of 9 male & 9 female mice were assigned to treatment groups as shown in the Table 3.

TABLE 3

Animal Treatment Groups

| Group No | Number of Mice | Gender | Test Article | Dose Level (infusion) µg/day |
|---|---|---|---|---|
| 1 | 3 | Male | Prolactin | 14 |
| 2 | 3 | Male | Human Chorionic Gonadotropin | 14 |
| 3 | 3 | Male | Control | 0 |
| 4 | 3 | Female | Prolactin | 14 |

TABLE 3-continued

Animal Treatment Groups

| Group No | Number of Mice | Gender | Test Article | Dose Level (infusion) µg/day |
|---|---|---|---|---|
| 5 | 3 | Female | Human Chorionic Gonadotropin | 14 |
| 6 | 3 | Female | Control | 0 |

18 Balb-C mice (8 male, 8 female, 18-22g and 8-12 weeks of age) were infused with prolactin or human chorionic growth subcutaneously using an alzet osmotic pump at 14 µg/day for 7 days. During the experiment animals had free access to water and food. The control group were infused with saline. Alzet micro-osmotic pump (Model 1007D) was used for introduction of the test compounds, either Human-Prolactin (Sigma L 4021, >97% SDS Page recombinant, expressed in *Escherichia coli* lyophilized powder, cell culture) or Chorionic gonadotropin Human (from human pregnancy urine, Sigma C0434). Both test compounds were dissolved in saline, with 300 µg of test compound dissolved is 255 µL saline (1.17 µg/µL) and 85 µL introduced into the pump for administration to the animal over the course of the study. The test compounds were administered, via the Alzet micro-osmotic pump through subcutaneous infusion. The animals were dosed with BrdU (Sigma- B5002, dissolved in 0.007% NaOH in phosphate buffer) 120 mg/kg intraperitoneally every 2 hr for 10 hr on day 7 and sacrificed 0.5 hr (or longer) after the last injections. At the end of the study animals are sacrificed and general necropsy is done. Heart, kidney and liver are collected for tissue analysis.

TABLE 4

Average BrdU positive cells per section of mouse tissue

| | | Saline | HCG | Prolactin |
|---|---|---|---|---|
| Heart | Male | 9.8 | 9.8 | 11 |
| | Female | 3.8 | 10 | 16.7 |
| Liver | Male | 12.8 | 32 | 9 |
| | Female | 37.6 | 74.6 | 14 |
| Kidney | Male | 32.7 | 46.7 | 31.3 |
| | Female | 75.3 | 430 | 60.3 |

Figure 2:
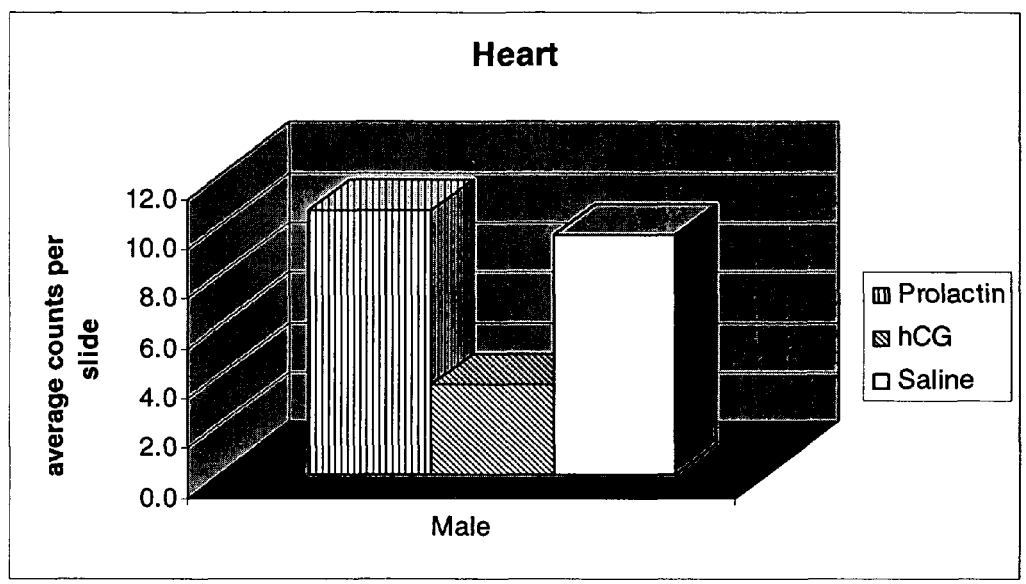
FIG. 2 shows the increase in average BrdU incorporation per slide observed in male mouse heart tissue sections.
Figure 3:
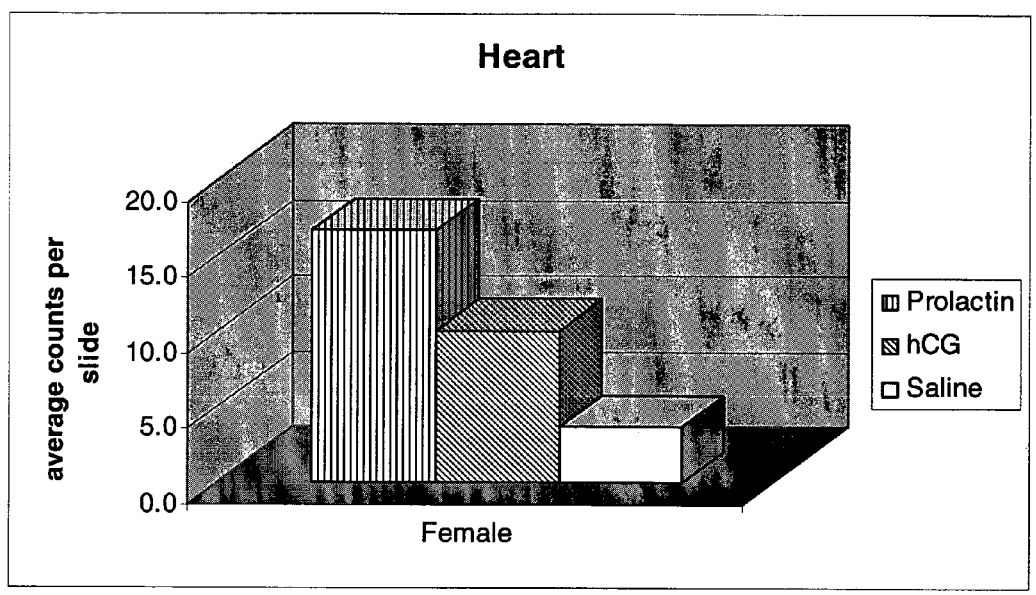
FIG. 3 shows the increase in average BrdU incorporation per slide observed in female mouse heart tissue sections.
Figure 4:
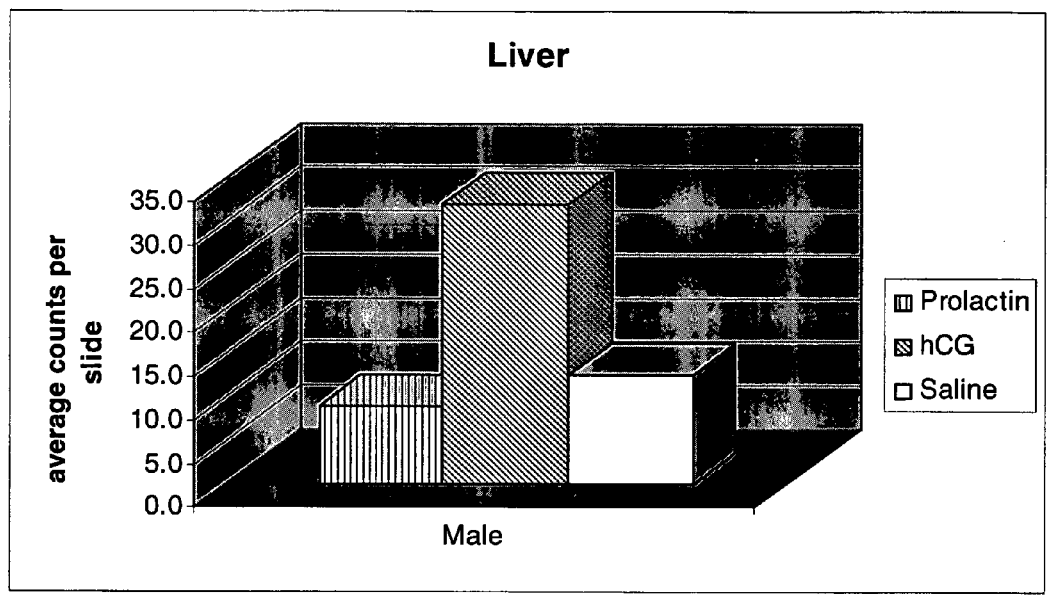
FIG. 4 shows the increase in average BrdU incorporation per slide observed in male mouse liver tissue sections.
Figure 5:
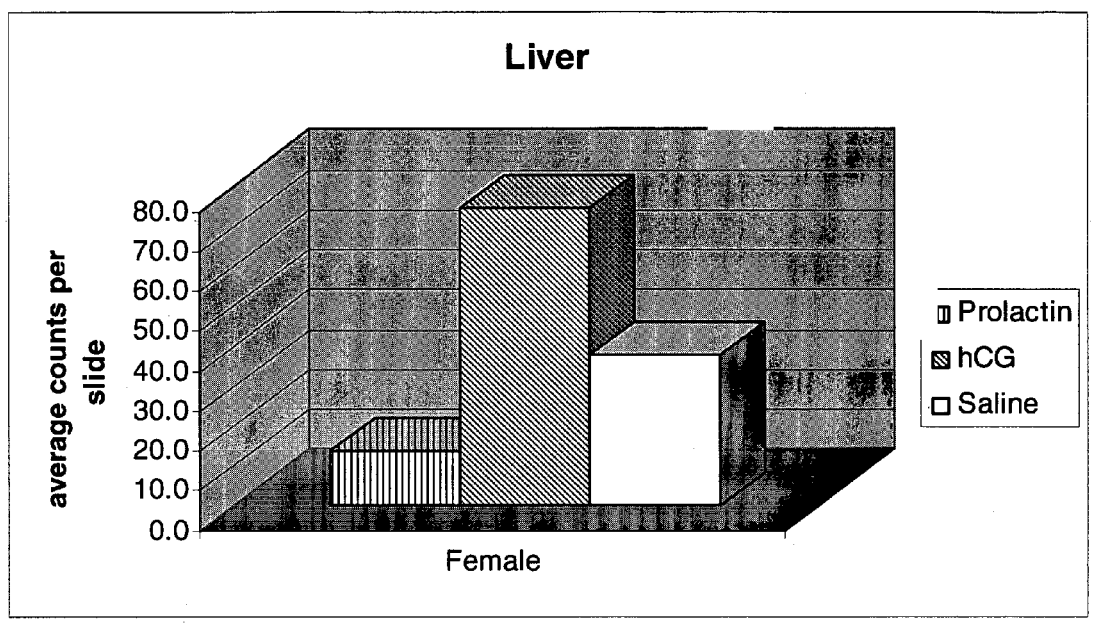
FIG. 5 shows the increase in average BrdU incorporation per slide observed in female mouse liver tissue sections.
Figure 6:
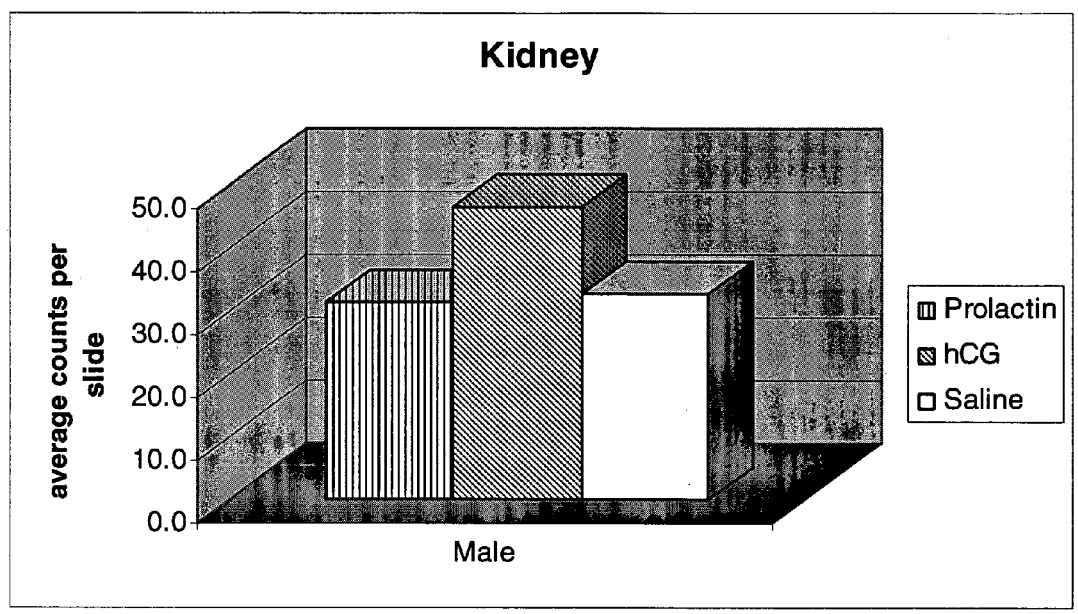
FIG. 6 shows the increase in average BrdU incorporation per slide observed in male mouse kidney tissue sections.
Figure 7:
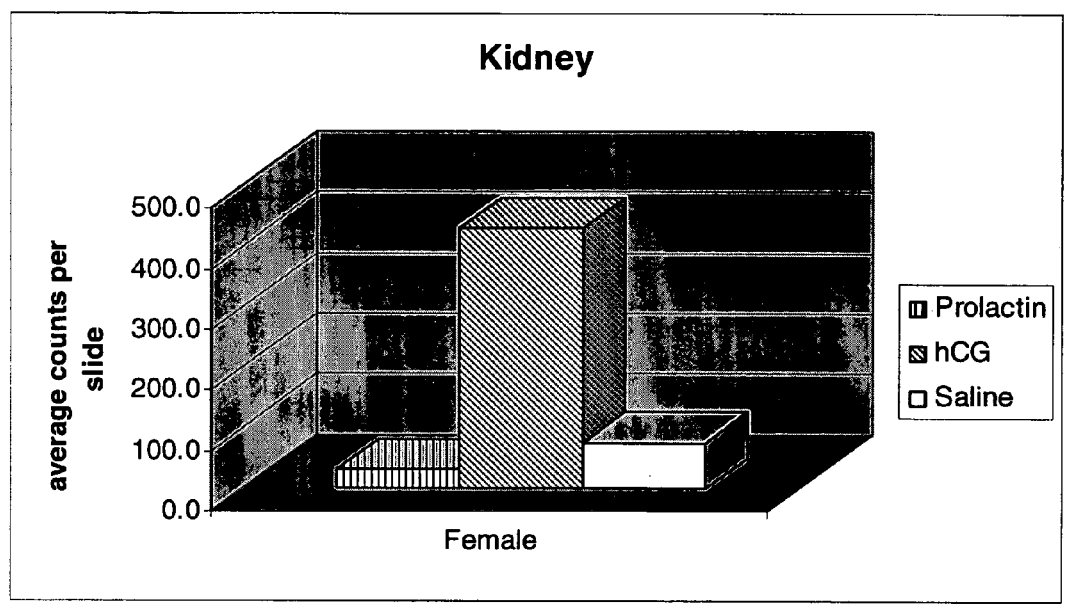
FIG. 7 shows the increase in average BrdU incorporation per slide observed in female mouse kidney tissue sections.

As can be seen in Table 4 and FIGS. 2 and 3, prolactin causes an increase in the uptake of BrdU in cells in heart tissue, consistent with an increase in stem cell proliferation or numbers in the heart tissue. This effect is most pronounced in females, which is specific for heart tissue and not observed in other tissues. It is contemplated that addition of prolactin to either male or female mice would cause greater increase in BrdU uptake, which correlates to an increased proliferation or number of stem cells present in the heart tissue. It is contemplated as part of the present invention that stimulation of proliferation or increased presence of stem cells in heart tissue of mice correlates with stimulation of proliferation or increased presence of stem cells in mammalian heart tissue in general, and human heart tissue in particular.

As can be seen in Table 4, and FIGS. 4 to 7, HCG, in either male or female mice, causes an increase in the uptake of BrdU in cells in liver or kidney tissue, consistent with an increase in stem cell proliferation or numbers in the liver or kidney tissue. It is contemplated that addition of HCG to either male or female mice would cause greater increase in BrdU uptake in the liver or kidney tissue, which correlates to an increased proliferation or number of stem cells present in the kidney or liver tissue. It is contemplated as part of the present invention that stimulation of proliferation or increased presence of stem cells in liver tissue of mice correlates with stimulation of proliferation or increased presence of stem cells in mammalian liver tissue in general, and human liver tissue in particular.

EXAMPLE 3

Stimulation of Proliferation of Pluripotential Stem Cells In Mice With Prolactin, HCG Or LH, Detected Through Stem-Cell Marker Presence Prolactin, HCG or LH is administered to normal healthy mice over a period of 3 to 14 days, with control mice administered normal saline of volume equal to the prolactin, HCG or LH. The mice are sacrificed and histological cross-sections of the heart, spleen, liver, retina, kidney and bone are taken and labelled with anti-CD44 antibodies. An increase in anti-CD44 antibody labelling is indicative of the presence of pluripotential stem cells. An increase in anti-CD44 antibody labelling in mice administered prolactin, HCG or LH, compared to control, is indicative of stimulation of pluripotential stem cell proliferation.

Although the above disclosure describes and illustrates various embodiments of the present invention, it is to be understood that the invention is not to be limited to these particular embodiments. Many variations and modifications will now occur to those skilled in the art. For a full definition of the scope of the invention, reference is to be made to the appended claims.

What is claimed is:

1. A method of treating a human with a disease or condition associated with damaged or diseased heart cells comprising selecting a subject with the disease or condition associated with damaged or diseased heart cells and administering stem cells to the subject with the damaged or diseased heart cells followed by, or preceded by, administering a compound selected from the group consisting of HCG and LH.

2. The method claim 1, wherein the compound is HCG.

3. The method of claim 1, wherein the compound is LH.

4. The method of claim 1, further comprising using an additional factor selected from the group consisting of follicle-stimulating hormone (FSH), gonadotropin releasing hormone (GnRH), prolactin releasing peptide (PRP), erythropoietin (EPO), pituitary adenylate cyclase activating polypeptide (PACAP), serotonin, bone morphogenic protein (BMP), epidermal growth factor (EGF), transforming growth factor alpha (TGFalpha), transforming growth factor beta (TGFbeta), fibroblast growth factor (FGF), estrogen, growth hormone, growth hormone releasing hormone, insulin-like growth factors, leukemia inhibitory factor, ciliary neurotrophic factor (CNTF), brain derived neurotrophic factor (BDNF), thyroid hormone, thyroid stimulating hormone, and platelet derived growth factor (PDGF).

5. The method of claim 4, wherein the additional factor is EPO.

6. A method to increase proliferation of cells in the heart in a patient in need thereof comprising administering to said patient a compound selected from the group consisting of HCG and LH and an additional factor selected from the group consisting of follicle-stimulating hormone (FSH), gonadotropin releasing hormone (GnRH), prolactin releasing peptide (PRP), erythropoietin (EPO), pituitary adenylate cyclase activating polypeptide (PACAP), serotonin, bone morphogenic protein (BMP), epidermal growth factor (EGF), transforming growth factor alpha (TGFalpha), transforming growth factor beta (TGFbeta), fibroblast growth factor (FGF), estrogen, growth hormone, growth hormone releasing hormone, insulin-like growth factors, leukemia inhibitory factor, ciliary neurotrophic factor (CNTF), brain derived neurotrophic factor (BDNF), thyroid hormone, thyroid stimulating hormone, and platelet derived growth factor (PDGF).

7. The method of claim 6, wherein the additional factor is EPO.

8. A method of treating a human with a disease or condition that has caused loss or death of cells in the heart of the human comprising administration of a dosage of HCG that is between 2000 international units (IU) and 10,000 (IU) to the human.

9. The method of claim 8, further comprising administering erythropoietin to the human.

10. A method of treating a human with a disease or condition that has caused loss of death of cells in the heart of the human comprising administration of HCG to the human.

11. The method of claim 10, further comprising administering erythropoietin to the human.

* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Glu His Trp Ser Tyr Leu Leu Arg Pro
1               5
```

```
<210> SEQ ID NO 2
<211> LENGTH: 31
<212> TYPE: PRT
<213> ORGANISM: Artificial Sequence
<220> FEATURE:
<223> OTHER INFORMATION: Synthetic Construct

<400> SEQUENCE: 2

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30
```